United States Patent [19]

Collins

[11] 4,002,073
[45] Jan. 11, 1977

[54] MOLTEN METAL SAMPLER

[76] Inventor: William J. Collins, 7005 Madison St., Merrillville, Ind. 46410

[22] Filed: July 11, 1975

[21] Appl. No.: 595,155

[52] U.S. Cl. .................. 73/425.4 R; 73/DIG. 9
[51] Int. Cl.² .................................. G01N 1/12
[58] Field of Search .............. 73/DIG. 9, 425.4 R

[56] References Cited
UNITED STATES PATENTS

| 3,656,350 | 4/1972 | Collins | 73/425.4 R |
| 3,693,449 | 9/1972 | Collins | 73/354 |
| 3,791,219 | 2/1974 | Falk | 73/425.4 R |
| 3,798,974 | 3/1974 | Boron | 73/425.4 R |
| 3,905,238 | 9/1975 | Falk | 73/425.6 |
| 3,915,014 | 10/1975 | Judge et al. | 73/425.6 |

FOREIGN PATENTS OR APPLICATIONS 6,804,930  10/1968  Netherlands ............ 73/DIG. 9

Primary Examiner—S. Clement Swisher

[57] ABSTRACT

The invention involves providing a device or sampler for obtaining a sample of a hot liquid, such as molten metal.

18 Claims, 25 Drawing Figures

U.S. Patent  Jan. 11, 1977  Sheet 2 of 2  4,002,073
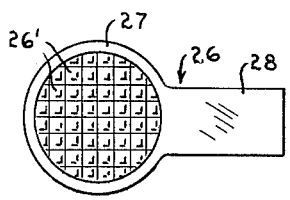
Fig.-11
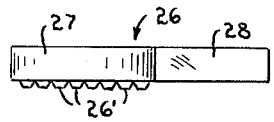
Fig.-12
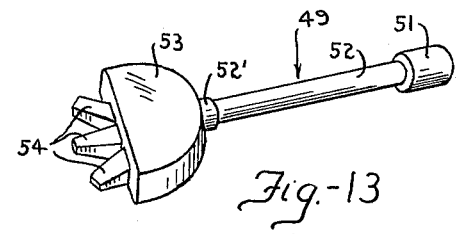
Fig.-13
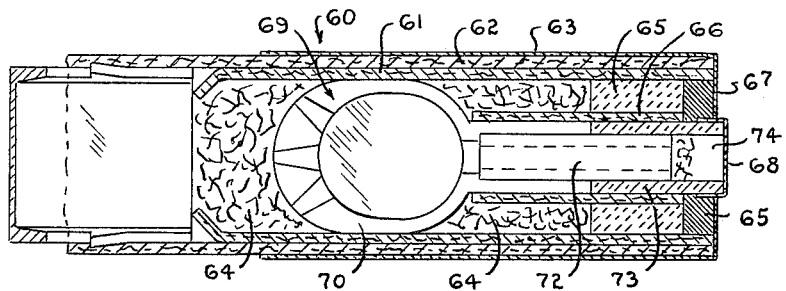
Fig.-14
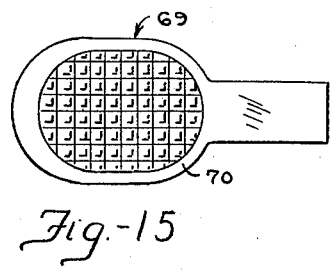
Fig.-15
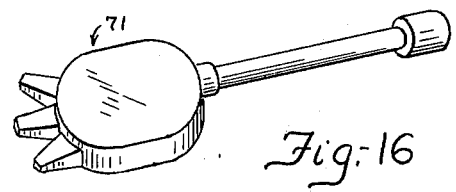
Fig.-16
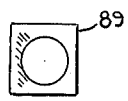
Fig.-20
Fig.-21
Fig.-25
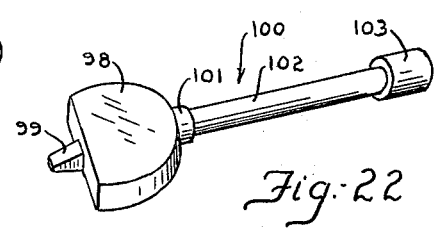
Fig.-22
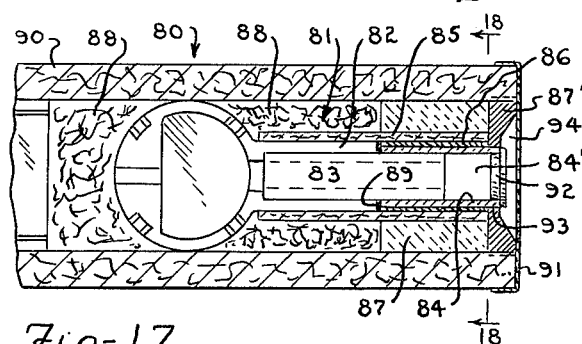
Fig.-17
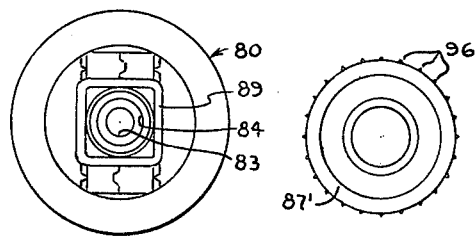
Fig.-18  Fig.-19
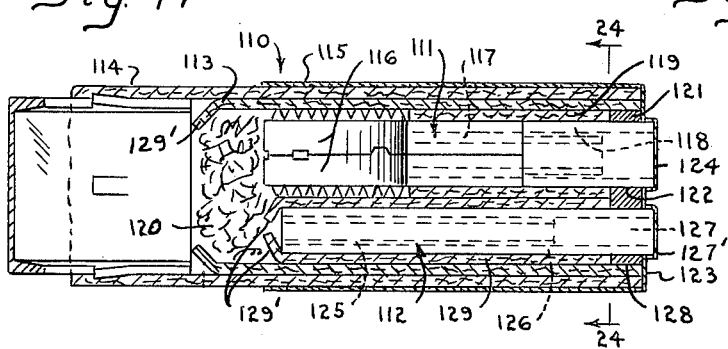
Fig.-23
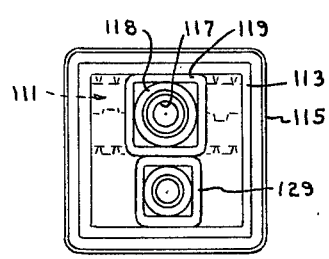
Fig.-24

MOLTEN METAL SAMPLER

BACKGROUND

A multitude of Patents have issued relative to obtaining samples of molten metal and quite a number appear to have utilized certain of the technology disclose in some of my Patents, such as for example, U.S. Pat. No. 3,415,124 dated Dec. 10, 1968 and U.S. Pat. No. 3,415,125 dated Dec. 10, 1968; at least to the extent of utilizing a pair of half sections which are constructed to provide a primary chamber for receiving a sample and a refractory tube carried by the sections for receiving molten metal for flow into the chamber.

The devices of the subject invention generally embody the above components and include certain additional elements with respect to design and construction as will appear hereinafter.

OBJECTIVES

One of the inportant objectives of the invention is to provide an elongated device comprising, among other things, an elongated casing, a support therein, wall structure which forms a primary chamber and a tubular extension constituting what may be termed one extremity of the device which is supported by the casing, a pair of telescopically connected refractory tubes which are communicatively connected to the chamber and may be considered to be an opposite extremity of the device which is carried by the support. Otherwise expressed, the opposite extremities of the device are preferably respectively supported by the casing and support at only longitudinally spaced locations within the confines of the casing whereby to assist in mounting the components in their correct operative relation to provide a stable device for use.

A significant objective of the invention is to provide a device of the above character which is preferably mounted in one end of an elongated housing or tube in such a way that after a sample is obtained the device may be readily released from the housing.

A particular object of the invention is to provide a device in which the half sections are provided with heat dissipating means and in which heat dissipating means of a different character is disposed in the casing and about portions of the device whereby to expedite and promote uniform cooling of the sample received.

Another object is to provide an improved mode of supporting or mounting the refractory tubes in the support and in which the support is so shaped that it serves to initially funnel or direct the molten metal into the tubes.

Also, an object is to provide structure comprising an elongated casing and a pair of dissimilar devices which are secured in the casing in a unique manner.

A specific object is to provide a device which includes an improved form of a shield or protector for the entrance end of the device.

A particular object of the invention is to provide a lance or wand of a unique character which can be readily assembled whereby to facilitate use of a device to promote safety or which can be readily disassembled for shipment or storage.

Another object is to provide an adapter for use with the lance and different forms of devices.

A specific objective is to provide a device of a particular shape or configuration whereby to facilitate entry of the device into a mass of molten metal and which minimizes erruption or splash when the device is introduced into the mass. Otherwise expressed, the device is rectangular cross-section compared to one which is round and offers appreciably less resistance to penetration of the molten metal and a sheath and/or shield substantially prevents erruption or splash, thereby affording protection to an operator.

Additional objects and advantages of the invention will become apparent after the description hereinafter set forth is considered in conjunction with the drawings annexed hereto.

DRAWINGS

Figure 9:
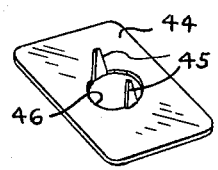
Figure 4:
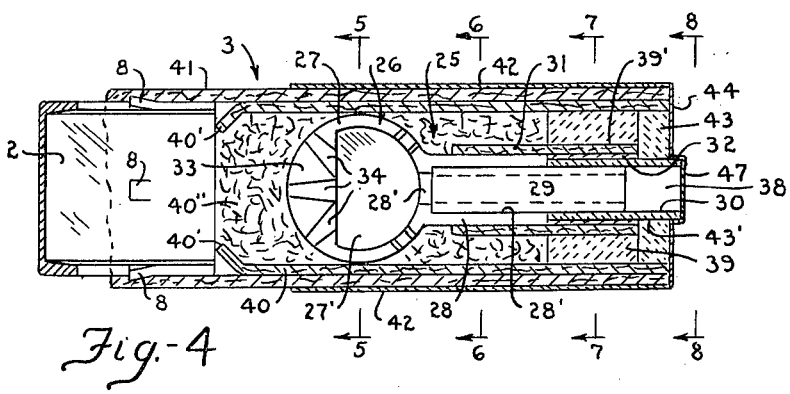
FIG. 4 is a partial horizontal section of the device shown in FIG. 3.
Figure 8:
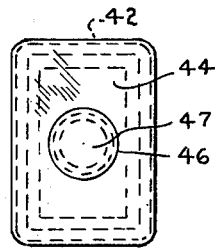
Figure 5:
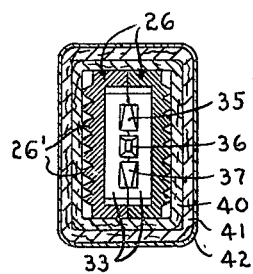
Figure 6:
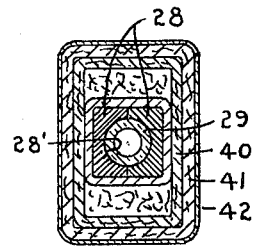
Figure 7:
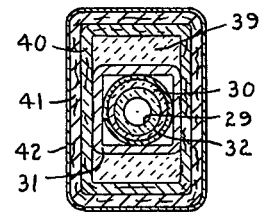

FIGS. 5, 6, and 7 are transverse sections taken substantially respectively on lines 5—5, 6—6, and 7—7 of FIG. 4 depicting various details of the structure;

FIG. 8 is an end view of the device looking in the direction of the arrows 8—8 of FIG. 4;

FIG. 9 is a perspective view of a modified closure or cap for use as a component of the device shown in FIG. 4;

FIG. 10 is a perspective view of an end member or plate constituting a shield of the device shown in FIG. 4;

FIGS. 11 and 12 are face and side views of one of a pair of half sections or wall structure forming means for receiving a sample of metal;

FIG. 13 is a perspective view of a solidified sample of metal obtained by the device;

FIG. 14 is a horizontal sectional view of a first modified device;

FIG. 15 is a face view of one of a pair of half sections of the device shown in FIG. 14;

FIG. 16 is a perspective view of a sample obtained by using the device shown in FIG. 14;

FIG. 17 is a horizontal sectional view of a second modified device;

FIG. 18 is a transverse section taken substantially on line 18—18 of FIG. 17;

FIG. 19, 20 and 21 are views of components of the device shown in FIG. 17;

FIG. 22 is a perspective view of a sample of metal obtained by utilizing the device illustrated in FIG. 17;

FIG. 23 is a horizontal section of a third modified device or structure having a pair of different receiving means for obtaining different forms of samples;

FIG. 24 is a transverse section taken substantially on line 24—24 of FIG. 23; and FIG. 25 is a perspective view of a sample obtained from one of the receiving means of FIG. 23 and 24.

DESCRIPTION

Reference is hereby made to my copending applications Ser. Nos. 543,687 filed Jan. 24, 1975; 563,590 filed Mar. 31, 1975; 563,581 filed Mar. 31, 1975 and 690,296 filed May 26, 1976 which disclose devices comprising, among other things, a secondary chamber or chambers which are described and/or defined in various ways.

Figure 1:
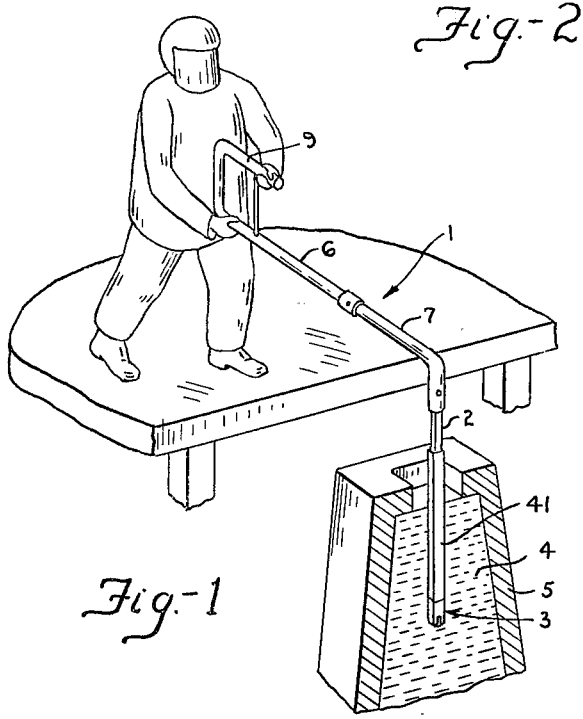
FIG. 1 is a perspective view of an operator utilizing a lance or wand for introducing a device carried thereby into a mass of molten metal for obtaining a sample therefrom.
Figure 2:
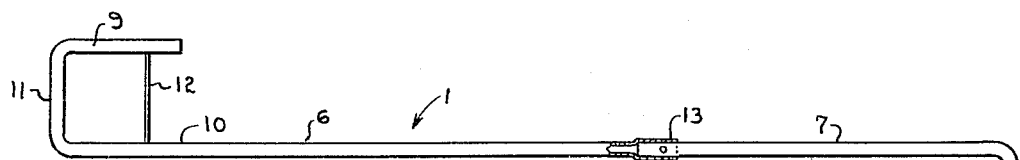
FIG. 2 is a side view of the lance shown in FIG. 1.
Figure 3:
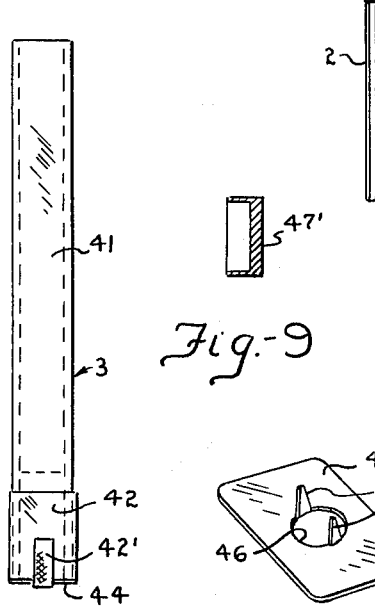
FIG. 3 is an elevational view of a device for obtaining a sample of molten metal.

Referring more particularly to FIG. 1 of the drawing there is shown an operator in the act of manipulating a lance or wand generally designated 1 carrying an adapter 2 which is adapted to be detachably connected to a device generally designated 3 of the character structurally depicted in FIGS. 4 through 12 for introduction into a mass of molten metal 4 contained in a vessel 5.

The lance 1 may be designed and constructed in various ways and it is believed to be unique in that it preferably comprises a plurality of sections which are adapted to be readily operatively connected for use or which may be disassembled to reduce space for storage or shipment.

More particularly, the lance comprises what may be termed an inner relatively long generally J-shaped tubular section 6, an intermediate tubular section 7 and an outer channel section constituting the adapter 2, The inner section 6 is provided with a relatively short portion 9 which is arranged in spaced parallel relation to a longer portion 10 of the section by a bridge portion 11, and a transverse brace 12 joins the portions 9 and 10. This inner structure may be considered an aft extremity or handle structure. The free end of section 6 is preferably expanded to provide a socket 13 for detachably receiving an inner end of the intermediate section 7 and the outer extremity of section 7 is preferably offset to provide a socket 14 rectangular in cross-section, for detachably accommodating an upper end of the adapter 2. This channel section includes a base wall and a pair of parallel side walls and each of these walls may be provided with an inclined portion, wedge or fastener 8 which serves to frictionally engage or connect with a housing of the device 3 for attaching the device to the adapter. The adapter 2 may be of any length desired for use with a device having a rectangular cross-section or it may be round in cross-section for reception in a component of a device having a circular cross-section as will be described more in detail subsequently.

The device 3 illustrated in FIG. 4 is sectioned as shown in FIGS. 5, 6 and 7 to disclose details of the structure and certain of the components of the device are also depicted in FIGS. 9 through 12. The device 3 may be designed and constructed in various ways but as shwon it is preferably comprised of what may be termed an elongated subassembly or unit generally designated 25 constituting means for receiving a sample of molten metal. More particularly this unit or means includes wall structure or a pair of mating half sections generally designated 26 which have enlarged recessed portions 27 and channel portions 28 forming an extended tubular formation, an inner refractory tube 29 and an outer refractory tube 30 telescopically connected to the inner tube so that the tubular formation and these tubes may be considered to constitute tubular structure through which molten metal may flow into a primary chamber or cavity 27' formed by the recessed portion 27 of the sections. The recessed portions 27 are preferably provided with external heat dissipating means in the form of outwardly extending integral portions 26' as depicted in FIGS. 5, 11 and 12.

The sub-assembly or unit 25 may also include a sleeve 31 of a sufficient length so that its inner extremity surrounds at least portions of the channel portions 28 of the half sections 26 and its outer extremity surrounds at least portions of the refractory tubes 29 and 30 and a sleeve 32 is preferably interposed between the sleeve 31 and the outer tube 30, all of which assists in holding the components assembled. The sleeve 32 surrounds the tube 30, abuts the tubular formation, and is preferably of a length substantially corresponding to the axial thickness of the support 39. It may be stated that the sleeves 31 and 32 constitute buffer means which serve to stabilize the operative relation between the components when the hot metal flows through the tubular structure into the primary and secondary chambers.

The half sections 26 may be constructed of any material suitable for the purpose but are preferably made from molded powdered metal. The enlarged portions 27 are generally round and have rims provided with mating projections and notches whereby to assist in correctly assembling the sections and these portions are also formed with relatively thick chordal end portions 33 preferably provided with radially extending tapered notches 34 which cooperate to define what may be termed three secondary chambers 35, 36 and 37 as evidenced in FIGS. 4 and 5 of the drawing. The mating projections and notches in the rims are so shaped that they provide vents for the primary chamber, as disclosed, for example, in my U.S. Pat. No. 3,552,214 dated Jan. 5, 1971.

The channel portions 28 of the half section are respectively provided with semi-cylindrical grooves which in combination define a cylindrical opening which receives the inner extremity of the tube 29 and the cross-dimensional factors of the grooves and the tube are preferably such that the tube is more or less clamped between the channel portions of the sections. The sections are also provided with mating notches at the junction between the enlarged and channel portions to provide an opening or passage 28' which has a diameter somewhat greater than the inside diameter of the tube 29 and with abutment means whereby to limit inward movement of the tube during its assembly in the sections and thereby locate an outer extremity of the tube a predetermined distance away from the channel portion 28.

The outer refractory tube 30 is preferably of a length so that its inner extremity surrounds the outer extremity of the inner tube 29 and its outer extremity projects outwardly a sufficient distance to form in combination with the tube 29 a relatively large cylindrical recess or entrance 38 which initially receives molten metal for successive flow into the primary chamber 27' and secondary chambers 35, 36 and 37 via the inner tube 29. If desired, a means such as a deoxidizing element, as shown, may be located in the entrance 38 for conditioning the inflowing metal, in which event, the entrance will also constitute a mixing chamber.

The unit 25, if so desired, may further include a relatively thick mounting, wall, partition, support or means 39 having an opening 39' therein through which the outer extremity of the unit extends for support. The thickness or axial dimension of the mounting or support, more or less, substantially corresponds to the axial dimensions of the outer extremities of the inner tube 29 and the sleeve 31 and the inner extremity of the outer tube 30 whereby to assist in stabilizing the operative relationship and stability of the components whereby to render the unit more resistant to shock when it receives the molten metal.

The unit 25 is preferably secured in an elongated tubular inner casing 40, which may be considered to be a component of the unit 25 and this casing is preferably confined in an elongated housing 41, and the latter is preferably protected by an outer sheath 42. This sheath is preferably of metal and of a length suitable to protect the outer extremity of the housing 41 when the device is introduced into the molten metal. It may be a piece of tubing rectangular in cross-section or it may be composed of a piece of channel sections secured together to form a tube. The outer marginal edges of the casing, housing, and sheath are preferably disposed in a flush relation and the mounting or support 39 is preferably inset in the casing 40 to provide a void which is preferably filled by a member, support, 1 mounting or means 43 and a plate constituting a shield 44 is preferably held against the aforesaid marginal edges and outer space of the support 43. Prongs 45 on the shield extend into an opening 43' provided in the support 43 and straddle the tube 30 whereby to assist in securing the shield in place. This shield is also provided with a center opening 46 through which the outer extremity of the outer tube 30 projects a relatively short distance beyond the outer face of the shield to facilitate entry of the molten metal. A metal cap 47 is press-fitted over the exposed end of the tube 30 and engages the shield 44. This cap has an end wall of a predetermined thickness. Metal caps having end walls of variable thicknesses may be utilized. For example, the cap 47' shown in FIG. 9 has a wall thickness greater than the cap 47. The thickness of the shield may be also varied. These variables are adjusted to take into consideration the variable temperatures of the same or different molten metals to be sampled. The caps serve to prevent, for example, scum from initially flowing into the entrance of the device when the latter is introduced into the molten metal, but melts in the virgin metal to allow the latter to flow into the device.

Attention is again directed to the fact that the device is of a substantially rectangular cross-section whereby to minimize resistance to the introduction of the device into the metal. Of further significance is the fact that the cross-sectional dimensions of the half sections 26 and casing 40 are preferably such that the enlarged or recessed portions 26 of the half sections 25 are snugly or frictionally held against inner opposed pairs of substantially parallel surfaces of the casing 40 as shown in FIG. 5 and that the sleeve 31 is frictionally held in the opening 39' of the support 39. More specifically, the inner extremity of the unit is supported in the casing at a rear location and its opposite or fore extremity is supported at a location spaced longitudinally forward of the rear location whereby to stabilize the relative operative positions of the components.

The inner casing 40 is also preferably provided with inner opposed inturned inclined portions 40' or abutments and these serve to retain a mass of fibrous non-inflammable material such as steel or fiber glass wool 40" in the casing and about the half sections, sleeve 31 and against the support 39. The portions 40' also serve as stops for limiting inward movement of the adapter 2 when the device is being connected to the adapter for obtaining a sample and/or in releasing or pushing the unit outwardly from the housing 41 after the device has retrieved a sample of molten metal. The adapter 2 is preferably in the form of a channel, as alluded to above, and is constructed for frictional detachable retention in the housing 41 as set forth above.

The various components comprising the device 3 illustrated in FIG. 4 may be constructed of any material suitable for the purpose. However, the sleeve 31 and sleeve 32, casing 40 and housing 41 are preferably made of pasteboard; the tube 29 and 30 of any suitable material such as quartz or Pyrex; the supports, mounting, or means 39 and 43 of suitable heat resistant or insulating material; and the sheath 42, shield 44 and cap 47 are preferably constructed of metal. However, the support 43 is preferably constructed from moulded powdered metal. If found desirable, those components which are rectangular in cross-section made be oval in cross-section.

The method of assembling the unit 25 is preferably accomplished by placing wool 40" into the casing 40, assembling the half-sections 26, inserting the tube 29 into the tubular formation 28 of the half sections, placing the tube 30 about the tube 29, the sleeve 32 about the tube 30, sliding the sleeve 31 over the sleeve 32 and about the tubular formation 28. Following this procedure the unit is inserted into the casing 40 so that the enlarged portions of the half sections are forcibly pressed against the wool. Additional wool is then inserted into the casing and about the unit as illustrated in FIG. 4, after which the supports 39 and 43 are successively placed in the casing. The unit is inserted into the housing 41, the sheath 42 about the housing and then the shield 44 and cap 47 are secured in place. If so desired, an adhesive may be applied to the outer surface of the casing 40 and/or the inner surface of the housing for fixedly securing them together, and a piece of tape 42' may be placed over the end of the device whereby to assist in holding the cap and shield in place.

The device is thus complete for detachable connection to the adapter 2 for use for immersion or introduction into the mass of molten metal by utilizing the lance 1, in which event, the cap 47, as noted above, will initially prevent the inflow of metal when passing through scum and then disintegrate to permit the inflow of virgin metal into the primary and secondary chambers for obtaining a relatively pure sample generally designated 49 as depicted in FIG. 13. This sample includes a cylindrical end portion 51 formed in the tube 30, a portion 52 formed in the tube 29, a portion 52' formed in the opening 28' adjacent the inner end of the tube 29, a relatively thick head portion 53 formed in the primary chamber 27' and three tapered radial portions 54 formed in the secondary chambers 35, 36 and 37. The relative sizes or cross-sectional dimensions of the aforesaid portions are predetermined whereby to facilitate analysis thereof and this is particularly true of the tapered portions 54 which are preferably of a size to obtain weights of substantially 1 gram each but may, if so desired, be of different cross-sectional dimensions to obtain portions having different weight values.

The sample 49 may be retrieved from the device, for example, by forcing the adapter 2 and/or the device toward one another to cause ejection of the unit 25 and/or device, whereupon the components thereof may be readily disassembled or broken apart to obtain the sample.

A first modified device, generally designated 60, is depicted in FIGS. 14 and 15 and will now be described. The device 60 is similar to the device 3 to the extent that it includes a casing 61, housing 62, sheath 63, wool 64, support or mountings 65 and 65', sleeve 66, shield 67 and a cap 68 which substantially respectively correspond to the casing 40, housing 41, sheath 42, wool 41″, supports 39 and 43, sleeve 32, shield 44 and cap 47.

The device 60 is also similar to the device 3 in that it is substantially rectangular in cross-section and includes a pair of half sections generally designated 69 which substantially correspond to the half sections 25 except for the fact that they have oblong, oval-shaped, or enlarged recessed portions 70 which in combination define a primary chamber of oval shape and radial tapered notches which form secondary chambers so that when the device 60 is introduced into a mass of molten metal a sample of the shape or configuration generally designated 71 in FIG. 16 will be obtained. In other words, the sample 71 substantially conforms to the sample 49 except that the head portion of the sample 71 is oval or oblong as compared to the round head portion 53 of the sample 49.

Referring more particularly to the device 60, the same also includes an inner refractory tube 72 having an inner extremity secured in a tubular formation formed by the half section 69, an outer refractory tube 73 having an inner extremity telescopically fitted about the outer extremity of tube 72 and against the tubular formation so that an outer extremity of the tube 73 projects outwardly beyond the tube 72 to provide an enlarged cylindrical recess, pocket or entrance 74. The sleeve 66, preferably of pasteboard, is secured in the support or mounting 65 and about the tube 73 and tubular formation of the half sections, but if so desired, this sleeve may be omitted, in which event the opening in the support would be made somewhat smaller so that the support would directly support the tube 73.

As depicted in FIG. 15 the enlarged or recessed oval portions of the half sections 69 are preferably provided with heat dissipating means corresponding to or similar to those provided on the half sections of the device 3.

A second modified device is disclosed in FIGS. 17 through 21 and generally designated 80 which is adapted to obtain a sample having a configuration or shape as depicted in FIG. 22.

More particularly, the device 80 includes a unit or sub-assembly generally designated 81 which comprises a pair of half sections 82, an inner refractory tube 83, an outer refractory tube 84, sleeves 85 and 86, a support or mounting 87, a support or means 87′ and wool 88 which generally respectively correspond to the half sections 26, tubes 29 and 30, sleeves 31 and 32, supports 39 and 43 and wool 40″ of the device 3 described above. However, there are several differences between the afore-mentioned components of the devices 3 and 80. For example, the half sections 82 are provided with only a pair of notches 80′ (one shown) which form a single secondary chamber as compared to the three chambers 35, 36 and 37 and a means constituting a buffer 89 which surrounds the inner tube 83 and is interposed between the tubular formation formed by the half sections and the inner ends of the outer tube 84 and sleeve 86 whereby to minimize any possible fracture or blow of the tubes when the molten metal flows into the device. The device 80 may also include an outer casing 90, a shield 91 and a cap 92. The means or support 87′ is disposed in the casing 90, against the outer marginal end edges of the sleeves 85 and 86 and outer face of the support 87. It should be noted that the shield 92 engages the end of the casing and has an annular flange encircling the casing. The support 87′ is provided with a central opening 93 through which an outer end of the outer tube 84 extends. A cap or plug 92, preferably in the form of a deoxidizing element is press-fitted into the end of the tube 84 may be employed to condition the inflowing metal prior to its reception in the chamber of the device. The outer face of the support 87′ is preferably provided with a counter-recess 94 whereby to promote or funnel the molten metal into an entrance or chamber 84′. The periphery of the disc or support 87′ is provided with radial projections or fins 96 which serve to bite into or intimately engage the inner surface of the casing 90 whereby to automatically secure the support in a correct position when pressed into the casing. The cap 92 is formed with an annular portion adapted for frictional fit in the outer tube 84 and with a flange portion for engaging the marginal end edge of this tube. The support 87′ may be made of molded powdered metal like the half sections or may be of any material suitable for the purpose. Also, if so desired, the supports 87 and 87′ may be constructed in one piece and the same is true of supports 39 and 43 and supports 65 and 65′.

Attention is directed to the fact that the casing 90 and supports 87 and 87′ are preferably round in cross-section; that the shield 91 is round; and that the sleeve 89 is preferably square in cross-section. Since the casing 90 is round, a different form of an adapter may be required for connecting the device 80 to the lance 1.

It should be noted that the outer end of the outer tube 84 preferably terminates at the base of the annular counter-recess 94 so that the latter, as alluded to above, serves to promote or funnel the entry of molten metal into the device. The primary chamber and secondary chambers formed by the half sections serve to respectively provide portions 98 and 99 of a sample generally designated 100, and the port or opening at the junction between the primary chamber and tubular portion of the sections forms a sample portion 101 and the tubes respectively form sample portions 102 and 103 for analysis. The secondary chamber is of a predetermined size or shape so that the portion 99 obtained therein is of a predetermined weight such as 1 gram.

A third modified structure is generally designated 110 and is exemplified in FIGS. 23 and 24 whereby different forms of samples may be obtained at substantially the same time. More particularly, the structure 110 comprises, among other things, a device or receiving means generally designated 111 for obtaining a sample, for example, similar to the sample shown in FIG. 13 and a device or receiving means generally designated 112 which serves to obtain a sample, for example, as shown in FIG. 25.

The devices 111 and 112 are preferably secured in a side-by-side relation within the confines of a tubular casing 113, the latter of which is like the casing 40 of the device 3. This casing is surrounded by a housing 114 and the latter by an outer metal jacket or sheath 115 which respectively correspond to those of device 3.

The device 111 comprises a pair of half sections 116, a pair of telescopically connected refractory tubes 117 and 118, and a sleeve 119, substantially square in cross-section and constructed of pasteboard is preferably disposed about the outer tube 118 and tubular formation of the half sections. Fibrous insulating material 120 is disposed in the casing 113. A support or member 121 is provided with a round opening 122 through which the outer tube 118 extends for support and its outer face is preferably located in a flush relation to the outer marginal end edges of the casing, housing, and sheath, and a shield 123 is secured against the aforesaid face and edges and is provided with a pocket or recess 124, which, as shown, receives the outer end of the outer tube 118. The sheath including the shield, as above referred to, penetrate the molten metal through the layer of scum and the shield disintegrates so that some of the molten metal may flow into the tubes 117 and 118 for reception in the primary chamber and secondary chambers formed by the half sections.

The device 112 preferably comprises an inner elongated refractory tube 125 and an outer refractory tube 126 having an inner extremity fitted over the outer end of the inner tube and an outer extremity which projects beyond the inner tube 125 to provide an enlarged cylindrical entrance 127 which initially receives the molten metal. The support 121 is provided with a round opening 128 through which the outer tube extends for support and the shield 123 is provided with an additional pocket or recess 127' for receiving the outer end of the outer tube, the latter of which extends a short distance in advance of the member 121 whereby to facilitate entry of the molten metal into the entrance 127.

The tubes 125 and 126 are secured in a casing 129 which is preferably square in cross-section and made of pasteboard. As shown in FIG. 24 an outer side of casing 129 engages one inner side of the casing 113 and an inner side of the casing 129 engages one side of the sleeve 119 and the heat dissipating means on the inner face of one of the half sections. An opposite side of the sleeve 119 engages an opposite side of the casing 113 and the heat dissipating means on the other half section engages an opposite side of the casing 113. The diametrically opposed peripheral surfaces of the enlarged or head portions of the half sections also engage opposed inner parallel surfaces of the casing 113, all for the purpose of locating and stabilizing the positions of the components. It should be noted that the casing 129 has an inner end provided with internal portions 129' which define a vent and stops for the tubes and that the wool 120 is located in the inner extremity of the casing 113 and is common to the devices 111 and 112 whereby to minimize outflow of metal therefrom. The sleeve 119 and casing 129 assist in holding certain of the components assembled and also serve as buffer means.

SUMMARY

In view of the foregoing it should be manifest that the various devices embody improved principles of design and construction whereby samples of molten metal can be expeditiously obtained. Of particular significance is the fact that the subassemblies or units of the devices are substantially supported only at their extremities but firmly in order to stabilize the units in a casing for use.

It will be evident that at least one of the devices includes tubular structure having an entrance for receiving molten metal and means operatively related to the entrance whereby the metal initially received is funneled into the entrance.

An important feature is to surround at least portions of the half-sections of each device with fibrous insulating material, such as steel or fiber-glass wool which serves to dissipate heat away from the half sections and thereby expedite cooling of a sample, as well as assist in minimizing outflow of metal from the secondary chambers.

Attention is particulary directed to the important fact that the devices are designed and constructed to protect an operator and that the lance is also constructed to promote safety.

Having thus described my invention, it is obvious that various modifications may be made in the same without departing from the spirit of the invention, and therefore, I do not wish to be understood as limiting myself to the exact forms, construction, arrangements, and combinations of parts herein shown and described.

I claim:

1. A device for obtaining a sample of hot liquid, said device comprising wall structure forming a primary chamber and a secondary chamber for successively receiving such a liquid, tubular structure extending from and communicatively connected to said primary chamber, a tubular casing substantially multisided in cross-section, surrounding and supporting said wall structure, a support fixed in said coating and provided with an opening, and said tubular structure being disposed in said opening and affording initial entry of a liquid for flow into said chambers.

2. The device defined in claim 1, including heat dissipating means disposed in said casing and about said wall structure.

3. The device defined in claim 1, including fibrous means disposed in said casing whereby to substantially prevent the outflow of liquid from said secondary chamber.

4. The device defined in claim 1, including an elongated tubular housing of non-circular cross-section which surrounds said casing and has an extremity extending therefrom for receiving an end of a lance.

5. The device defined in claim 1, including a second support disposed in said casing providing additional support for said tubular structure.

6. The device defined in claim 1, in which said tubular structure comprises a pair of telescopically connected tubes and one of these tubes has an outer end providing an entrance for initially receiving the liquid, and said support supports said outer end adjacent said entrance.

7. The structure defined in claim 1, including a plurality of different forms of closures which are so constructed that any one thereof can be applied to said tubular structure for temporarily preventing the entry of liquid therein.

8. The device defined in claim 1, in which said wall structure also forms additional secondary chambers for receiving liquid from said primary chamber.

9. A device for obtaining a sample of molten metal, said device comprising wall structure forming a chamber for receiving a sample, a tubular casing surrounding and supporting said wall structure, a support secured in said casing and provided with an opening, elongated tubular structure communicatively connected to said chamber and extending into said opening for carriage by said support and having an entrance for initially receiving the molten metal, an external shield protecting said support and provided with an aperture affording access to said entrance, a closure for normally closing said entrance, and elongated means carried by said casing for connection with a lance so that the device may be inserted into a mass of molten metal in a manner whereby said closure will melt and allow metal to enter said entrance and flow into said chamber via said tubular structure.

10. A device for obtaining a sample of molten metal, said device comprising an elongated tubular casing, an elongated unit having an enlarged inner extremity comprising wall structure provided with a primary chamber and an outer tubular extremity through which molten metal may flow into said chamber, said wall structure also being provided with a secondary chamber for receiving metal from said primary chamber, means disposed in said casing serving to resist the outflow of metal from said secondary chamber, a partition secured in a fore end of said casing and provided with an opening, said casing and said inner extremity of said unit having cross-sectional dimensions whereby said inner extremity is supported by said casing at a rear location and said tubular extremity extends into said opening for support by said partition at a forward location spaced longitudinally from said rear location for correctly positioning and holding said unit in said casing.

11. The device defined in claim 10, in which said outer tubular extremity is multi-sided in cross-section.

12. The device defined in claim 10, in which said chamber is formed by a pair of mating sections, and a mass of fibrous heat dissipating material substantially surrounds said sections.

13. The device defined in claim 10, including a tubular housing which surrounds said casing, a sheath surrounds at least a portion of said housing, a shield serves to protect said partition, and a closure for said tubular extremity.

14. The device defined in claim 10, including abutment means provided on said casing for engagement by a member whereby to facilitate release of said unit from said casing after a sample of molten metal has been obtained.

15. The device defined in claim 10, including a member which is secured in said casing against said partition and is provided with an opening through which said tubular extremity extends, and a shield is secured in relation to an outer face of said member and provided with an opening through which said tubular extremity extends.

16. The device defined in claim 10, in which said chamber is formed by a pair of mating sections, said tubular extremity includes portions of said sections and a pair of telescopically connected tubes, a first sleeve surrounds at least portions of said sections whereby to assist in holding them assembled, and a second sleeve surrounds at least a portion of one of said tubes.

17. A device for obtaining a sample of molten metal, said device comprising a casing, structure forming a chamber and a tubular extension, a first tube having an inner portion secured in said extension and an outer portion extending therefrom, a second tube having an inner portion surrounding said outer portion of said first tube and an outer portion providing an entrance for initially receiving molten metal for flow into said chamber via said tubes, a support secured in said casing and having an opening through which said second tube extends, a sleeve disposed in said opening and about said second tube, a shield secured in relation to said support and provided with an opening through which said second tube extends, and a closure normally closing said entrance.

18. The device defined in claim 17, including a mass of non-inflammable wool disposed in said casing and substantially surrounding said structure and tubular extension thereof.

* * * * *